(12) United States Patent
Dihora et al.

(10) Patent No.: US 10,154,947 B2
(45) Date of Patent: *Dec. 18, 2018

(54) ANTIPERSPIRANT COMPOSITION

(71) Applicant: The Procter & Gamble Company, Cincinnati, OH (US)

(72) Inventors: Jiten Odhavji Dihora, Liberty Township, OH (US); Timothy Roy Nijakowski, Mason, OH (US); Jonathan Robert Cetti, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 155 days.

This patent is subject to a terminal disclaimer.

(21) Appl. No.: 14/989,610

(22) Filed: Jan. 6, 2016

(65) Prior Publication Data

US 2017/0189281 A1    Jul. 6, 2017

(51) Int. Cl.

| | |
|---|---|
| *A61K 8/11* | (2006.01) |
| *A61K 8/26* | (2006.01) |
| *A61K 8/73* | (2006.01) |
| *A61Q 13/00* | (2006.01) |
| *A61Q 15/00* | (2006.01) |
| *A61K 8/55* | (2006.01) |

(52) U.S. Cl.
CPC ............... *A61K 8/11* (2013.01); *A61K 8/26* (2013.01); *A61K 8/55* (2013.01); *A61K 8/553* (2013.01); *A61K 8/732* (2013.01); *A61Q 13/00* (2013.01); *A61Q 15/00* (2013.01); *A61K 2800/31* (2013.01); *A61K 2800/56* (2013.01); *A61K 2800/596* (2013.01); *A61K 2800/652* (2013.01)

(58) Field of Classification Search
None
See application file for complete search history.

(56) References Cited

U.S. PATENT DOCUMENTS

| | | | |
|---|---|---|---|
| 5,250,290 A | 10/1993 | Giacomoni et al. | |
| 5,931,994 A | 8/1999 | Mateo Herrero | |
| 6,117,915 A * | 9/2000 | Pereira | A61K 8/062 424/59 |
| 6,248,703 B1 | 6/2001 | Finucane et al. | |
| 6,344,488 B1 | 2/2002 | Chenite et al. | |
| 6,608,017 B1 * | 8/2003 | Dihora | C11D 3/124 424/490 |
| 9,732,303 B2 * | 8/2017 | Dihora | C11B 9/00 |
| 9,803,157 B2 * | 10/2017 | Cetti | C11B 9/00 |
| 2002/0160040 A1 | 10/2002 | Spicer et al. | |
| 2004/0157761 A1 | 8/2004 | Man et al. | |
| 2005/0197276 A1 | 9/2005 | Rigley et al. | |
| 2005/0220750 A1 | 10/2005 | Robert et al. | |
| 2005/0249805 A1 | 11/2005 | Holsztynska | |
| 2006/0094617 A1 | 5/2006 | Price et al. | |
| 2006/0263435 A1 | 11/2006 | Davis et al. | |
| 2008/0085297 A1 | 4/2008 | Dave et al. | |
| 2009/0047309 A1 | 2/2009 | Maes et al. | |
| 2010/0112043 A1 | 5/2010 | Takeuchi et al. | |
| 2010/0203122 A1 | 8/2010 | Weyer et al. | |
| 2011/0197782 A1 | 8/2011 | Wang et al. | |
| 2012/0165410 A1 | 6/2012 | Dodd et al. | |
| 2012/0202694 A1 | 8/2012 | Dodd et al. | |
| 2012/0237578 A1 * | 9/2012 | Lei | B01J 13/18 424/401 |
| 2014/0072617 A1 | 3/2014 | Dumas et al. | |

FOREIGN PATENT DOCUMENTS

| | | |
|---|---|---|
| EP | 0 850 564 A1 | 7/1998 |
| WO | WO 93/09176 | 5/1993 |
| WO | WO 2005/084710 A2 | 9/2005 |
| WO | WO 2006/037230 A1 | 4/2006 |
| WO | WO 2007/027711 A1 | 3/2007 |
| WO | WO 2009/123764 A2 | 10/2009 |
| WO | WO 2009/155115 A2 | 12/2009 |
| WO | WO 2010/140987 A1 | 12/2010 |
| WO | WO 2014/025977 A1 | 2/2014 |

OTHER PUBLICATIONS

U.S. Appl. No. 14/989,526, filed Jan. 6, 2016, Jonathan Robert Cetti et al.
U.S. Appl. No. 14/989,547, filed Jan. 6, 2016, Jiten Odhavji Dihora et al.
U.S. Appl. No. 14/989,589, filed Jan. 6, 2016, Jiten Odhavji Dihora et al.

* cited by examiner

*Primary Examiner* — Bethany P Barham
*Assistant Examiner* — Dominic Lazaro
(74) *Attorney, Agent, or Firm* — Kathleen Y. Carter; Carrie A. Morgan

(57) ABSTRACT

An antiperspirant composition including a starch delivery vehicle which includes a starch, a core material, and a lipophilic phosphate ester, wherein the lipophilic phosphate ester at least partially coats the core material.

9 Claims, No Drawings

ANTIPERSPIRANT COMPOSITION

FIELD OF THE INVENTION

The present disclosure generally relates to antiperspirant composition including a starch benefit agent delivery vehicles.

BACKGROUND OF THE INVENTION

Delivery vehicles are often used within products to release a benefit agent based on a mechanism, like friction or moisture. However, given the large variety of formulations for products, there is room for improvement in the variety of delivery vehicles.

SUMMARY OF THE INVENTION

An anhydrous antiperspirant composition including an antiperspirant active, and a starch delivery vehicle, including a starch, a benefit agent, and a lipophilic phosphate ester; wherein the lipophilic phosphate ester at least partially coats the benefit agent.

An anhydrous antiperspirant composition comprising an antiperspirant active, and a starch delivery vehicle including a starch, a perfume, and a lipophilic phosphate ester; wherein the lipophilic phosphate ester at least partially coats the perfume and the perfume is miscible with the lipophilic ester.

An antiperspirant composition including an antiperspirant active, and a starch perfume delivery vehicle including an octenylsuccinic acid anhydride modified starch, a perfume, and an octyl phosphate ester, wherein the octyl phosphate ester at least partially coats the perfume and is a reaction product of the octyl phosphate ester and a multivalent ion, and wherein the perfume is miscible in the octyl phosphate ester.

These and additional elements and combinations will be more fully understood in light of the description below.

DETAILED DESCRIPTION OF THE INVENTION

Definitions

"Microcapsule" as used herein refers to the resulting structure of the at least partial coating of a core material with a phosphate ester.

"Starch delivery vehicle" as used herein refers to the resulting structure from incorporation of a microcapsule into a starch matrix.

Encapsulation of a material is often a way to protect the material from its environment, where, without such protection the material may degrade or its presence may not be noticeable to a consumer. Starch is often used as an encapsulation material. Starch can act as a matrix which can trap a material and then allow release of that material upon exposure to a trigger, like moisture.

Previous uses of starch as a matrix and encapsulate shell materials have suffered from drawbacks, particularly, the leakage of materials from the matrix into the composition into which they are mixed. The early release of materials from a starch matrix may be better than not utilizing a starch matrix at all, but would be even better if the leakage could be reduced.

The present inventors discovered that coating of materials prior to inclusion in a starch matrix can help to reduce leakage of the materials from the starch. For example, see Table A below, showing a perfume oil control and a starch encapsulated non-coated perfume oil versus a starch encapsulated perfume oil coated with a phosphate ester. The coated perfume oil encapsulated in the starch had a much lower leakage of the perfume from the starch into the leave-on conditioner formulation when aged for one week at 40° C. In addition, the coated perfume oil encapsulated in the starch performed better in the hexane test, where hexane is expected to extract only the non-encapsulated oil. Thus, it also appears that more of the perfume is encapsulated within the starch matrix when combined with the phosphate ester coating. Moreover, the coated perfume oil encapsulated in starch also had a significantly lower extraction level in the ethanol test, where ethanol is expected to extract both the free and encapsulated perfume. Without being limited by theory, it is believed that at least partially coating a material, like perfume, with a material, like a phosphate ester, helps to prevent diffusion of the perfume; helps to enhance the amount of perfume encapsulated in a starch; and can serve to protect the perfume once encapsulated from extraction.

TABLE A

| Sample Description | % hexane extractable perfume oil | % ethanol extractable perfume oil | 1 wk/40° C. Leakage in leave-on conditioner formulation (%) |
|---|---|---|---|
| Perfume Oil Control | 100% | 100% | 100% |
| Starch Encapsulated Perfume Oil | 100% | 100% | 100% |
| Starch Encapsulated Perfume Oil with Phosphate Ester | 23% | 82% | 52% |

Encapsulating a material, like a perfume oil, is not necessarily a straight forward exercise. In fact, here, it was approached like the making of a microcapsule. Thus, interfacial oil-in-water polymerization was used. Interfacial oil-in-water polymerization utilizes an aqueous phase, and a lipophilic phase comprising the core material, dispersed in the lipophilic phase. Upon mixing of a suitable lipophilic phase with an aqueous phase, a distinct phase boundary can occur between the two phases and an inorganic containing microcapsule shell wall can be formed along the phase boundary, at least partially coating the core material.

Microcapsules

Several properties are desirable in a phosphate ester to successfully form microcapsules that at least partially coat a material for use in a starch delivery vehicle. These properties include solubility in a lipophilic phase, insolubility in an aqueous phase, and stability with core materials. Solubility in a lipophilic phase and insolubility in an aqueous phase can contribute to the partitioning of the phosphate ester at an oil/water interface so that a microcapsule can form versus emulsifying into the aqueous phase which would not allow the formation of a microcapsule.

Suitable phosphate esters, and salts thereof, can include phosphate monoesters, phosphate diesters, or a mixture thereof. Chemical formulas of phosphate monoesters and phosphate diesters are depicted in Formulas I and II respectively, each of which are reproduced below:

Formula I

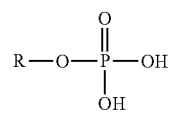

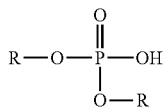

Formula II

As can be appreciated, phosphate esters can be formed from alcohols, ethoxylated alcohols, or ethoxylated phenols with the R-group of each such phosphate ester determined by the specific alcohol, ethoxylated alcohol, or ethoxylated phenol used to form the phosphate ester. The specific identity of an R-group can influence the properties of a phosphate ester compound and can, for example, determine the solubility of the phosphate ester in aqueous or lipophilic solutions and can influence whether the phosphate ester emulsifies or partitions along the phase boundary when exposed to an aqueous phase.

Phosphate esters exhibiting lipophilicity can be, for example, phosphate esters formed from certain alcohols. For example, the R-group of such phosphate alcohol esters can have a carbon chain length between about 6 carbon atoms and about 18 carbon atoms, and going further can be a $C_8$ to $C_{10}$ linear alkyl chain. As can be appreciated, such R-groups can allow a phosphate ester to be soluble in a lipophilic phase, insoluble in an aqueous phase, and partition at an oil/water interface with the R-groups arranging to face the core materials and the alcohol group(s) facing the aqueous phase. R-groups smaller than about 6 carbons in length can be insoluble in lipophilic solutions while R groups larger than about 18 carbon atoms can prevent the phosphate ester from migrating to the oil-water interface upon exposure to an aqueous solvent.

Although, phosphate esters formed of ethoxylated alcohols and ethoxylated phenols can also be lipophilic, most such phosphates esters can also be water soluble and can, as a consequence, act as a surfactant. Such surfactant-like phosphate esters can be unsuitable for a coating of a material as disclosed herein because such phosphate esters can form stable oil-in-water emulsions preventing the formation of an interfacial oil/water partition necessary for the formation of a coating on the material, like a microcapsule.

As can be appreciated, suitable phosphate esters should be unreactive with the materials to be encapsulated. For example, a phosphate ester can be unsuitable if it chemically bonds to the core materials, causes an acid/base reaction with the materials, causes precipitation of the materials, or otherwise negatively affects the materials. Examples of suitable phosphate esters that do not react with the core materials can include phosphate esters having a low acid value such as phosphate esters having an acid value below about 950 mg KOH/g in certain examples, and phosphate esters having an acid value between about 190 mg KOH/g and about 450 mg KOH/g in certain examples.

As noted herein, suitable phosphate esters can include phosphate monoesters, phosphate diesters, or mixtures thereof. For example, the phosphate esters can include a 1:1 ratio of phosphate monoesters and phosphate diesters. It can be advantageous to include relatively larger ratios of a phosphate diester in comparison to phosphate monoester, or to include only a phosphate diester. As can be appreciated, a phosphate diester can exhibit lower acidity than a comparable phosphate monoester and can also exhibit a higher crosslinking density since the single crosslinking site is more likely to be used for crosslinking. Exemplary phosphate esters can include hexadecyl phosphate, heptyl nonyl phosphate, octyl phosphate, and combinations thereof.

The core materials of a microcapsule as disclosed herein can vary widely. Generally, suitable core materials can be selected from any material that is miscible with the selected phosphate esters. Advantageously however, phosphate esters can be miscible with both polar and non-polar materials which can allow for a wider variety of core materials to be encapsulated than with other known microencapsulation architectures. The ability to encapsulate both polar and non-polar compounds can also eliminate the need to use a partitioning modifier to modify the polarity of the core materials. For example, menthol can be encapsulated using certain microencapsulation processes disclosed herein despite being a polar compound. Generally, a suitable core material can instead be selected on the basis of its C log P value which generally indicates lipophilicity of a compound. Suitable core materials can have a C log P value of about 0 or greater, a C log P value of about 1 to about 5, or a C log P value of about 3 to about 4.5.

Illustrative examples of core materials that can be encapsulated can include, but are not limited to, perfumes; brighteners; insect repellants; silicones; waxes; flavors; vitamins; fabric softening agents; skin care agents; enzymes; probiotics; dye polymer conjugates; dye clay conjugates; perfume delivery systems; odor masking agents, odor absorbers, sensates, pheromones; anti-bacterial agents; dyes; pigments; bleaches; flavorants; sweeteners; pharmaceuticals; fertilizers; herbicides and mixtures thereof.

As discussed above, the core material can be a perfume oil. As can be appreciated, encapsulation of a perfume oil can allow for products and compositions including the microcapsules to have a controlled release of the perfume oil. The perfume oil can both slowly release over time due to degradation of the microcapsules but can also be desirably released in greater quantities during certain activities that cause rupturing of the microcapsules. For example, an antiperspirant composition including microcapsules as disclosed herein can provide a continuous release of perfume oil throughout the day and can release larger doses of perfume during physical activities that cause rupturing of the microcapsules due to, for example, physical shear forces and elevated heat. Examples of suitable perfume oils, and their C log P values, are depicted in Table 1.

TABLE 1

| Perfume Oils | CAS Number | ClogP Value | Boiling Point, (° C.) |
|---|---|---|---|
| 3,6-Nonadien-1-ol | 53046-97-2 | 2.5 | 213 |
| Allyl Caproate | 123-68-2 | 3.0 | 198 |
| Allyl Heptoate | 142-19-8 | 3.6 | 216 |
| Beta Gamma Hexenol | 928-96-1 | 1.3 | 155 |
| Cis 3 Hexenyl Acetate | 3681-71-8 | 2.2 | 167 |
| Cis-6-Nonen-1-OL FCC | 35854-86-5 | 2.7 | 214 |
| Cyclo Galbanate | 68901-15-5 | 2.5 | 273 |
| Cymal | 103-95-7 | 3.6 | 290 |
| Dihydro Myrcenol | 18479-58-8 | 3.1 | 195 |
| Dimethyl Benzyl Carbinyl Butyrate | 10094-34-5 | 4.1 | 270 |
| Ethyl 2 Methyl Pentanoate | 39255-32-8 | 2.6 | 157 |
| Ethyl Acetoacetate | 141-97-9 | 0.2 | 179 |
| Ethyl Caproate FCC | 123-66-0 | 2.6 | 165 |
| Ethyl Maltol | 4940-11-8 | 0.2 | 274 |
| Ethyl Oenanthate | 106-30-9 | 3.2 | 183 |
| Ethyl-2-Methyl Butyrate | 7452-79-1 | 1.9 | 133 |
| Florhydral | 125109-85-5 | 3.6 | 295 |
| Hexamethylindanopyran | 1222-05-5 | 5.4 | 398 |
| Gamma Decalactone | 706-14-9 | 3.2 | 211 |
| Hexyl Acetate | 142-92-7 | 2.6 | 165 |

TABLE 1-continued

| Perfume Oils | CAS Number | ClogP Value | Boiling Point, (° C.) |
|---|---|---|---|
| Ionone Beta | 14901-07-6 | 4.0 | 267 |
| Jasmolactone | 32764-98-0 | 2.4 | 219 |
| Liffarome | 67633-96-9 | 2.1 | 167 |
| Ligustral Or Triplal | 68039-49-6 | 1.8 | 199 |
| Linalool | 78-70-6 | 2.4 | 204 |
| Melonal | 106-72-9 | 2.1 | 182 |
| Nectaryl | 95962-14-4 | 4.2 | 319 |
| Para Hydroxy Phenyl Butanone | 5471-51-2 | 1.6 | 294 |
| Pino Acetaldehyde | 33885-51-7 | 3.0 | 261 |
| Prenyl Acetate | 1191-16-8 | 1.1 | 145 |
| Thesaron | 22471-55-2 | 3.8 | 216 |
| Undecalactone | 104-67-6 | 3.8 | 228 |
| Undecavertol | 81782-77-6 | 3.1 | 242 |
| Verdox | 88-41-5 | 3.9 | 223 |
| Verdural B Extra | 41519-23-7 | 3.2 | 193 |

As discussed above, the formation of a microcapsule that at least partially coats the core material can include an interfacial polymerization process. During such process there can be a lipophilic phase, a first aqueous phase, and a second aqueous phase.

A lipophilic phase contains the core material and the phosphate ester. The core material can be a minor or major constituent of the lipophilic phase. For example, the core materials can form about 0.01% to about 99% percent of the lipophilic phase, about 40% to about 95% of the lipophilic phase, or from about 60% to about 90% of the lipophilic phase. The phosphate ester can be, for example, from about 2% to about 20%, by weight of the lipophilic phase, or from about 2% to about 12%, by weight of the lipophilic phase.

The core materials can be encapsulated within an insoluble shell wall formed by precipitation of the phosphate ester with a multivalent ion. A multivalent ion can reside in an aqueous phase. As can be appreciated, upon addition of the lipophilic phase to an aqueous solution, small droplets of the lipophilic phase can form in the aqueous phase with phosphate esters arranged at the oil-water phase boundary of each droplet. Multivalent ions present in the aqueous phase can then cause precipitation of the phosphate ester. The core materials can have very low solubility with phosphate ester salts leading to a microcapsule of very low permeability.

A variety of suitable multivalent ions can be included in an aqueous phase. For example, calcium chloride, aluminum sulfate, aluminum sulfate, chitosan, polyethyleneimine ("PEI") and polydiallyldimethylammonium chloride ("poly-DADMAC") are non-limiting examples of suitable multivalent ions that can cause precipitation of a phosphate ester. A multivalent ion may be present in an amount of about 1% to about 5%, by weight of the aqueous phase.

An interfacial polymerization process can also include a second aqueous phase. Starch or a modified-starch such as octenylsuccinic acid anhydride ("OSAN") modified starch, can be included in the second aqueous phase. Starches suitable for use can be made from raw starch, pregelatinized starch, modified starch derived from tubers, legumes, cereal and grains for example corn starch, wheat starch, rice starch, waxy corn starch, oat starch, cassava starch, waxy barley starch, waxy rice starch, sweet rice starch, amioca, potato starch, tapioca starch and mixtures thereof. Modified starches may be particularly suitable for use in the present invention, and these include hydrolyzed starch, acid thinned starch, starch having hydrophobic groups, such as starch esters of long chain hydrocarbons (C5 or greater), starch acetates, starch octenyl succinate and mixtures thereof.

Starch esters, particularly starch octenyl succinates are especially preferred. Starch can provide various improvements to the microcapsules as disclosed herein. For example, starch can act as a strengthening component of a microcapsule shell wall, can act as a crosslinking agent to improve the strength of a microcapsule, and can act as a dehydrating agent to remove water after formation of a microcapsule. Starch can be present in the second aqueous phase in an amount of about 20% to about 70%, by weight of the second aqueous phase.

When starch is included in a second aqueous phase, the aqueous phase including starch can be first mixed with a lipophilic phase before addition of the multivalent ion aqueous phase. Upon mixing of the starch phase and lipophilic phase, a matrix of starch can encapsulate the lipophilic droplets formed of phosphate ester and the core materials. Later addition of the multivalent ion aqueous phase can then cause precipitation of the phosphate ester and formation of the low permeability inorganic shell wall resulting in a perfume core contained within a phosphate ester shell, contained within a starch matrix.

After formation of the starch delivery vehicle, it can be dried and converted to a powder through industry standard drying processes. For example, the delivery system can be dried utilizing suitable spray drying apparatus. Drying of the microcapsules can allow for easier incorporation into anhydrous products forms, like antiperspirants.

As can be appreciated, the permeability of microcapsules as disclosed herein can be controlled in certain examples though selection and control of various processes such as, for example, selection of the wall materials, selection of the phosphate esters, and the time and temperature of the manufacturing processes. For example, a microcapsule formed using only phosphate diester compounds can exhibit less permeability than a similar microcapsule formed from a similar phosphate monoester compound due to the greater degree of crosslinking possible in the phosphate diester compound. Without being limited be theory, it is believed that the use of polyethyleneimine as a multivalent ion can lead to more fragile microcapsules due to the Lewis acid and Lewis base interactions between the polyethyleneimine and the phosphate ester. Varying these conditions can allow the microcapsules to rupture more easily upon exposure to moisture or humidity.

Starch delivery vehicles can be incorporated into an antiperspirant and/or deodorant composition comprising an adjunct ingredient.

Antiperspirant/Deodorant Composition

For example, a starch delivery vehicle may be incorporated into a deodorant or antiperspirant composition. Adjunct ingredients for a deodorant or antiperspirant can include, for example, a deodorant active, an antiperspirant active, a carrier, or a combination thereof. Antiperspirant and deodorant compositions can be, for example, a soft solid, a solid, or an aerosol. The composition can be anhydrous.

Antiperspirant Active

The compositions can include an antiperspirant active suitable for application to human skin. The concentration of the antiperspirant active in the antiperspirant composition should be sufficient to provide the desired enhanced wetness protection. For example, the active can be present in an amount of from about 0.1%, about 0.5%, about 1%, or about 5%; to about 60%, about 35%, about 25% or about 20%, by weight of the antiperspirant composition. These weight percentages are calculated on an anhydrous metal salt basis exclusive of water and any complexing agents such as glycine, glycine salts, or other complexing agents.

An antiperspirant active can include any compound, composition, or other material having antiperspirant activity. Such actives can include astringent metallic salts, like inorganic and organic salts of aluminum, zirconium and zinc, as well as mixtures thereof. For example, the antiperspirant active can include zirconium-containing salts or materials, such as zirconyl oxyhalides, zirconyl hydroxyhalides, and mixtures thereof; and/or aluminum-containing salts such as, for example, aluminum halides, aluminum chlorohydrate, aluminum hydroxyhalides, and mixtures thereof.

1. Aluminum Salts

Aluminum salts useful herein can include those that conform to the formula:

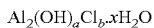

$Al_2(OH)_aCl_b \cdot xH_2O$ wherein a is from about 2 to about 5; the sum of a and b is about 6; x is from about 1 to about 6; where a, b, and x can have non-integer values. For example, aluminum chlorohydroxides referred to as "5/6 basic chlorohydroxide," wherein a is about 5 and "2/3 basic chlorohydroxide", wherein a=4 can be used.

A general description of these aluminum salts can be found in Antiperspirants and Deodorants, Cosmetic Science and Technology Series Vol. 20, 2nd edition, edited by Karl Laden. Mixtures of aluminum salts are described in British Patent Specification 1,347,950, filed in the name of Shin et al. and published Feb. 24, 1974.

2. Zirconium Salts

Zirconium salts useful herein can include those which conform to the formula:

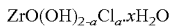

$ZrO(OH)_{2-a}Cl_a \cdot xH_2O$ wherein a is from about 1.5 to about 1.87; x is from about 1 to about 7; and wherein a and x can both have non-integer values. These zirconium salts are described in Belgian Patent 825,146, issued to Schmitz on Aug. 4, 1975. Useful to the present invention are zirconium salt complexes that additionally contain aluminum and glycine, commonly known as "ZAG complexes". These complexes can contain aluminum chlorohydroxide and zirconyl hydroxy chloride conforming to the above-described formulas. Examples of two such complexes include aluminum zirconium trichlorohydrex and aluminum zirconium tetrachlorohydrex.

The antiperspirant active can comprise, for example, aluminum zirconium tetrachlorohydrex glycine; aluminum zirconium tetrachlorohydrate, aluminum zirconium pentachlorohydrate, aluminum zirconium pentachlorohydrex glycine, aluminum zirconium trichlorohydrex glycine, aluminum zirconium trichlorohydrate, aluminum zirconium octachlorohydrate, aluminum zirconium octachlorohydrex glycine, aluminum chlorohydrate, aluminum chlorohydrex polyethylene glycol, aluminum dichlorohydrate, aluminum dichlorohydrex polyethylene glycol, aluminum dichlorohydrex propylene glycol, aluminum sesquichlorohydrate, aluminum sesquichlorohydrex polyethylene glycol, aluminum sesquichlorohydrex propylene glycol or a combination thereof.

Carrier

The composition can also include a carrier. The carrier can be present, for example, at concentrations ranging from about 10%, about 15%, about 20%, about 25%; to about 99%, about 70%, about 60%, or about 50%, by weight of the composition. Such concentrations will vary depending upon variables such as product form, desired product hardness, and selection of other ingredients in the antiperspirant composition. The carrier can be any anhydrous carrier known for use in antiperspirant or deodorant compositions or otherwise suitable for topical application to the skin. For example, anhydrous carriers can include, but are not limited to, volatile and nonvolatile fluids.

A. Volatile Fluid

The compositions can also include a volatile fluid such as a volatile silicone carrier. Volatile fluids are present, for example, at concentrations ranging from about 20% or from about 30%; to about 80%, or no about 60%, by weight of the composition. The volatile silicone of the solvent can be cyclic, linear, and/or branched chain silicone. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976).

The volatile silicone can be a cyclic silicone. The cyclic silicone can have from about 3 silicone atoms, or from about 5 silicone atoms; to about 7 silicone atoms, or to about 6 silicone atoms. For example, volatile silicones can be used which conform to the formula:

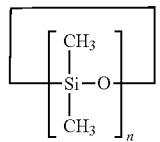

wherein n is from about 3, or from about 5; to about 7, or to about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

B. Non-Volatile Fluid

A non-volatile fluid can also be present, for example, at concentrations ranging from about 1%, from about 2%; to about 20%, or about 15%, by weight of the composition.

1. Non-Volatile Organic Fluids

The non-volatile organic fluid can be present at concentrations ranging from about 1%, from about 2% but no more than about 20% or no more than about 15%, by weight of the composition.

Non-limiting examples of nonvolatile organic fluids include, but are not limited to, mineral oil, PPG-14 butyl ether, isopropyl myristate, petrolatum, butyl stearate, cetyl octanoate, butyl myristate, myristyl myristate, C12-15 allylbenzoate (e.g., Finsolv™), dipropylene glycol dibenzoate, PPG-15 stearyl ether benzoate and blends thereof (e.g. Finsolv TPP), neopentyl glycol diheptanoate (e.g. Lexfeel 7 supplied by Inolex), octyldodecanol, isostearyl isostearate, octododecyl benzoate, isostearyl lactate, isostearyl palmitate, isononyl/isononoate, isoeicosane, octyldodecyl neopentanoate, hydrogenated polyisobutene, and isobutyl stearate. Many such other carrier liquids are disclosed in U.S. Pat. No. 6,013,248 (Luebbe et al.) and U.S. Pat. No. 5,968,489 (Swaile et al.).

2. Nonvolatile Silicone Fluids

The composition can also include a non-volatile silicone fluid. The non-volatile silicone fluid can be a liquid at or below human skin temperature, or otherwise in liquid form within a antiperspirant composition, like an anhydrous antiperspirant composition, during or shortly after topical application. The concentration of the non-volatile silicone can be from about 1%, from about 2%; to about 15%, about 10%, by weight of the composition. Nonvolatile silicone fluids can include those which conform to the formula:

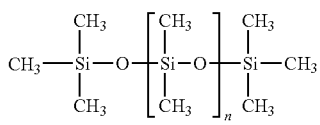

wherein n is greater than or equal to 1. These linear silicone materials can generally have viscosity values of from about 5 centistokes, from about 10 centistokes; to about 100,000 centistokes, about 500 centistokes, about 200 centistokes, or about 50 centistokes, as measured under ambient conditions.

Specific non limiting examples of suitable nonvolatile silicone fluids include Dow Corning 200, hexamethyldisiloxane, Dow Corning 225, Dow Corning 1732, Dow Corning 5732, Dow Corning 5750 (available from Dow Corning Corp.); and SF-96, SF-1066 and SF18(350) Silicone Fluids (available from G.E. Silicones).

Low surface tension non-volatile solvent can be also be used. Such solvents can be selected from the group consisting of dimethicones, dimethicone copolyols, phenyl trimethicones, alkyl dimethicones, alkyl methicones, and mixtures thereof. Low surface tension non-volatile solvents are also described in U.S. Pat. No. 6,835,373 (Kolodzik et al.).

Structurants

Antiperspirant or deodorant compositions can also include a structurant to help provide the composition with the desired viscosity, rheology, texture and/or product hardness, or to otherwise help suspend any dispersed solids or liquids within the antiperspirant composition. The term "structurant" can include any material known or otherwise effective in providing suspending, gelling, viscosifying, solidifying, or thickening properties to the composition or which otherwise provide structure to the final product form. Non-limiting examples of structurants include, for example, gelling agents, polymeric or nonpolymeric agents, inorganic thickening agents, or viscosifying agents. Non-limiting examples of thickening agents include, for example, organic solids, silicone solids, crystalline or other gellants, inorganic particulates such as clays or silicas, or combinations thereof.

The concentration and type of the structurant selected for use in the antiperspirant composition can vary depending upon the desired product form, viscosity, and hardness. The thickening agents suitable for use herein, can have a concentration range from about 0.1%, about 3%, or about 5%; to about 35%, about 20%, or about 10%, by weight of the composition. Soft solids will often contain a lower amount of structurant than solid compositions. For example, a soft solid can contain from about 1.0% to about 9%, by weight of the composition, while a solid composition can contain from about 15% to about 25%, by weight of the antiperspirant composition, of a structurant. This is not a hard and fast rule, however, as a soft solid product with a higher structurant value can be formed by, for example, shearing the product as it is dispensed from a package.

Non-limiting examples of suitable gelling agents include fatty acid gellants, salts of fatty acids, hydroxyl acids, hydroxyl acid gellants, esters and amides of fatty acid or hydroxyl fatty acid gellants, cholesterolic materials, dibenzylidene alditols, lanolinolic materials, fatty alcohols, triglycerides, sucrose esters such as SEFA behenate, inorganic materials such as clays or silicas, other amide or polyamide gellants, and mixtures thereof. Optionally, the microcapsules can be premixed with such gellants prior to incorporation into the antiperspirant composition.

Suitable gelling agents include fatty acid gellants such as fatty acid and hydroxyl or alpha hydroxyl fatty acids, having from about 10 to about 40 carbon atoms, and ester and amides of such gelling agents. Non-limiting examples of such gelling agents include, but are not limited to, 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred gelling agents are 12-hydroxystearic acid, esters of 12-hydroxystearic acid, amides of 12-hydroxystearic acid and combinations thereof.

Other suitable gelling agents include amide gellants such as di-substituted or branched monoamide gellants, mono-substituted or branched diamide gellants, triamide gellants, and combinations thereof, including n-acyl amino acid derivatives such as n-acyl amino acid amides, n-acyl amino acid esters prepared from glutamic acid, lysine, glutamine, aspartic acid, and combinations thereof. Other suitable amide gelling agents are described in U.S. Pat. No. 5,429,816, issued Jul. 4, 1995, and U.S. Pat. No. 5,840,287, filed Dec. 20, 1996.

Still other examples of suitable gelling agents include fatty alcohols having at least about 8 carbon atoms, at least about 12 carbon atoms but no more than about 40 carbon atoms, no more than about 30 carbon atoms, or no more than about 18 carbon atoms. For example, fatty alcohols include but are not limited to cetyl alcohol, myristyl alcohol, stearyl alcohol and combinations thereof.

Non-limiting examples of suitable triglyceride gellants include tristearin, hydrogenated vegetable oil, trihydroxystearin (Thixcin® R, available from Rheox, Inc.), rape seed oil, castor wax, fish oils, tripalmitin, Syncrowax® HRC and Syncrowax® HGL-C(Syncrowax® available from Croda, Inc.).

Other suitable thickening agents include waxes or wax-like materials having a melt point of above 65° C., more typically from about 65° C. to about 130° C., examples of which include, but are not limited to, waxes such as beeswax, carnauba, bayberry, candelilla, montan, ozokerite, ceresin, hydrogenated castor oil (castor wax), synthetic waxes and microcrystalline waxes. The synthetic wax can be, for example, but not limited to, a polyethylene, a polymethylene, or a combination thereof. Some suitable polymethylenes can have a melting point from about 65° C. to about 75° C. Examples of some suitable polyethylenes include those with a melting point from about 60° C. to about 95° C. Other high melting point waxes are described in U.S. Pat. No. 4,049,792, Elsnau, issued Sep. 20, 1977.

Further structurants for use in the antiperspirant compositions can include inorganic particulate thickening agents such as clays and colloidal pyrogenic silica pigments. For example, but not limited to, colloidal pyrogenic silica pigments such as Cab-O-Sil®, a submicroscopic particulated pyrogenic silica can be used. Other known or otherwise effective inorganic particulate thickening agents that are commonly used in the art can also be used in the antiperspirant compositions described herein. Concentrations of particulate thickening agents can range, for example, from about 0.1%, about 1%, or about 5%; to about 35%, about 15%, about 10% or about 8%, by weight of the composition.

Clay structurants include montmorillonite clays, non-limiting examples of which include bentonites, hectorites, and colloidal magnesium aluminum silicates. These and other clays can be hydrophobically treated, and when treated will generally be used in combination with a clay activator. Non-limiting examples of suitable clay activators include propylene carbonate, ethanol, and combinations thereof. When clay activators are present, the amount of clay activator can be in a range of from about 40%, about 25%, or about 15%; to about 75%, about 60%, or about 50%, by weight of the clay.

Surfactant

The compositions can include a surfactant. A surfactant is generally present at a level of about 0.05% to about 5%, by weight of the composition, but can contain, from about 0.5% to about 5.0%; from about 1.0% to about 4%; from about 1.5% to about 3.5%; from about 1.75% to about 2.5%; about 2%, or any combination thereof. The surfactant can have a HLB range of about 2 to about 14; about 6 to about 12; about 8 to about 10; or any combination thereof. The surfactant can be free of polyoxyethylene sorbitan fatty acids. The surfactant can comprise, for example, a $C_{20-40}$ Pareth-10. Another suitable surfactant is a nonionic ethoxylated linear alcohol with a carbon chain length of 20-40. Suitable surfactants include PERFORMATHOX™ 450 ethoxylate.

Propellant

The composition can be in the form of an aerosol. Thus, the composition can include a propellant and be stored in a spray device. The spray device can comprise a propellant stored in one or more reservoirs of the container. The propellant may be stored in the same reservoir as an antiperspirant composition or a separate reservoir, although it is preferred that the propellant is stored within the same reservoir as the antiperspirant composition. The propellant may be present in a liquefied form that is miscible with liquid carriers of the antiperspirant composition as well as gaseous state within a head space of the reservoir. The liquid propellant and the antiperspirant composition form a mixture that travels through the container, eventually exiting the container where the liquid propellant vaporizes to from a spray. The propellant may have a concentration from about 25% to about 90%, or from about 40% to about 85%, or from about 50% to about 80%, by weight of the composition.

A wide variety of propellants may be used with the spray devices and antiperspirant compositions described herein, although in some embodiments the spray device is substantially free of compressed gas propellants such as nitrogen, air and carbon dioxide. Some suitable propellants may have a boiling point (at atmospheric pressure) within the range of from about −45° C. to about 5° C. Some suitable propellants may include chemically-inert hydrocarbons such as propane, n-butane, isobutane and cyclopropane, and mixtures thereof, as well as halogenated hydrocarbons such as dichlorodifluoromethane (propellant 12) 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), dimethyl ether and monochlorodifluoromethane, and mixtures thereof. Some propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), HFO1234 (trans-1,3,3,3-tetrafluoropropene) and 152A (1,1 difluoroethane).

Other Materials

The compositions can also include other materials known for use in antiperspirant, deodorant or other personal care products, including those materials that are known to be suitable for topical application to skin. Non-limiting examples include dyes or colorants, emulsifiers, distributing agents, pharmaceuticals or other topical actives, skin conditioning agents or actives, deodorant agents, antimicrobials, preservatives, surfactants, processing aides such as viscosity modifiers and wash-off aids.

EXAMPLES

Example 1

To study the suitability of various phosphate esters in coating core materials, various compositions Samples A to I were produced, each containing a perfume oil and a different phosphate ester in a 9:1 perfume to phosphate ester ratio. As depicted in Table 2, each Sample was added to deionized water, 10% weight aluminum sulfate, and 10% weight polyDADMAC, to evaluate the formation of an oil/water interface, as well as the formation of any precipitates. The phosphate esters were commercially obtained from Lakeland Labs Ltd.

TABLE 2

| Sample | Phosphate Ester (Lakeland Labs Ltd.) | Monoester/Diester | Acid Value (mg KOH/g phosphate ester) |
|---|---|---|---|
| A | PPE-1614 Phosphate Phenol Ethoxylate Ester | Mono and Di | 180 |
| B | PAE-803 Phosphate Alcohol Ethoxylate Ester | Mono and Di | 190 |
| C | PAE-136 Phosphate Alcohol Ethoxylate Ester | Mono and Di | 200 |
| D | PAE-147 Phosphate Alcohol Ethoxylate Ester | Mono | 220 |
| E | PA-900 Phosphate Alcohol Ester | Mono and Di | 275 |

TABLE 2-continued

| Sample | | | |
|---|---|---|---|
| F | PA-604 Phosphate Phenol Ethoxylate Ester | Mono | 320 |
| G | PA-800 Phosphate Alcohol Ester | Mono and Di | 360 |
| H | PA-400 Phosphate Alcohol Ester | Mono and Di | 460 |
| I | PA-100 Phosphate Alcohol Ester | Mono | 950 |

| Sample | Perfume/Phosphate Ester 90/10 Behavior in Water | Perfume/Phosphate Ester 90/10 Behavior in 10 wt. % Aluminum Sulfate | Perfume/Phosphate Ester 90/10 Behavior in 10 wt. % polyDADMAC | Result |
|---|---|---|---|---|
| A | Part of oil sinks to bottom; after agitation, all oil floats to top | Precipitate observed | Oil droplets surrounded by a white colored precipitate; droplets appear to be stabilized | Dissolves into aqueous phase (emulsifier) |
| B | Precipitate and stable emulsion | Precipitate observed, stable milky white emulsion | White precipitate observed | Dissolves into aqueous phase (emulsifier) |
| C | Precipitate and stable emulsion | Precipitate observed | White precipitate observed | Dissolves into aqueous phase (emulsifier) |
| D | Precipitate and stable emulsion | Precipitate observed, stable milky white emulsion | White precipitate observed | Dissolves into aqueous phase (emulsifier) |
| E | No precipitate, individual oil particles don't coalesce | Precipitate observed; oil phase viscosity increased; irregularly shaped oil droplet floating on top of water | Viscous paste | Soluble in perfume oil, precipitate at interface, does not dissolve into aqueous phase |
| F | Precipitate and stable emulsion | Immediate precipitate observed | Droplets appear to be stabilized | Dissolves into aqueous phase (emulsifier) |
| G | No precipitate, one coalesced oil droplet on top of water | No precipitate observed | Droplets appear to be stabilized | Soluble in perfume oil; no precipitate at oil-water interface |
| H | Oil sinks to bottom; after agitation, floats to top | Precipitate observed | Droplets appear to be stabilized | Dissolves into aqueous phase (emulsifier) |
| I | 90% of oil sinks to bottom and becomes a ball surrounded by white precipitate. After agitation, oil remains on bottom and coalesces into one drop | White precipitate observed surrounding droplet of oil | White precipitate observed | Reacts with perfume oil to form a dark brown solution, precipitation observed |

As depicted by Table 2, Sample E formed of a phosphate alcohol ester exhibited the best results. Specifically, Sample E was miscible with a perfume oil, did not dissolve into the aqueous phase, and formed precipitates with both the aluminum sulfate solution and the polyDADMAC solution at the oil-water interface.

Example 2

Example 2 is a Comparative Example of a spray dried microcapsule formed without a phosphate ester. Example 2 is formed through the preparation of several solutions:

Solution A was prepared by mixing 40.12 grams of aluminum sulfate (Sigma Lot SLBF0512V) to deionized water (Omnipur 98072052) to obtain a homogeneous, transparent solution.

Solution B was prepared by mixing 124.5 grams of octenyl succinic acid anhydride modified starch (HICAP 100, Ingredion Lot DCI6638) into 370.5 grams of water at preheated to 70 degrees Celsius. Next, 6.5 grams of 4,5-imidazolidine-3-one (Sigma) was added, followed by 2.61 grams of ammonium chloride (Sigma).

Solution C was prepared by slowly adding 52 grams of perfume oil to 462.5 grams of Solution B at a temperature of 25° C., and then homogenizing said mixture for 3 minutes at 24,000 RPM using an Ultra Turrax T25 mixer. 47 grams of Solution A was then added with mixing.

The resultant Solution D was then pumped into a Niro spray dryer, 3 ft diameter, centrifugal wheel atomizer, with co-current airflow that has an inlet air temperature of 200° C. The flow of Solution D into the spray dryer was manipulated to achieve an outlet air temperature between 95° C. and 105° C. The approximate dry basis composition of the spray dried particle is depicted in Table 3 below.

TABLE 3

| Material | Weight Percentage |
| --- | --- |
| HICAP 100 Starch | 67.1% |
| Al2(SO4)3 | 2.7% |
| Perfume | 30.2% |
| Phosphate Ester | 0% |
| % Yield from Dryer | 85% |

Example 3

Example 3 is an Inventive Example of a starch delivery vehicle formed with a shell wall incorporating a phosphate ester and surrounding a core material which is then captured in a starch matrix. Example 3 was formed from the following solutions:

Solution A was prepared by mixing 40.12 grams of aluminum sulfate (Sigma Lot SLBF0512V) with 250 g deionized water (Omnipur 98072052) to obtain a homogeneous, transparent solution.

Solution B was prepared by mixing 50.02 grams of phosphate ester PA-900 (Lakeland Laboratories Ltd) in 202.4 grams of perfume oil.

Solution C was prepared by mixing 124.5 grams of octenyl succinic acid anhydride modified starch (HICAP 100) into 370.5 grams of water preheated to 70° C. Next, 6.5 grams of 4, 5-imidazolidine-3-one (Sigma) was added, followed by 2.61 grams of ammonium chloride (Sigma).

Solution D was prepared by slowly adding 72.5 grams of Solution B to 462.5 grams of Solution C at a temperature of 25° C., and homogenizing for 3 minutes at 24,000 RPM using an Ultra Turrax T25 mixer. Subsequently, 52 grams of Solution A was then added with mixing. Solution D was then pumped into a Niro spray dryer, 3 ft diameter, centrifugal wheel atomizer, with co-current airflow that has an inlet air temperature of 200° C. The flow of Solution D into the spray dryer was manipulated to achieve an outlet air temperature between 95° C. and 105° C. The approximate dry basis composition of the spray dried particle is depicted in Table 4 below.

TABLE 4

| Material | Weight Percentage |
| --- | --- |
| HICAP 100 Starch | 59.4% |
| $Al_2(SO_4)^3$ | 2.7% |
| Perfume | 30.3% |
| Phosphate Ester | 7.6% |
| % Yield from Dryer | 87% |

Example 3 was analyzed by Cryo-SEM to better understand particle morphology and understand elemental distribution across the surface of the microcapsules. Two types of particles were observed: smooth surface particles that are highly spherical and particles with a wrinkled surface with dents. Both particles exhibited similar elemental compositions. Aluminum and phosphate were found on every capsule (the elemental analysis penetration depth was about 1 micron, and the particle size is on the order of 20 microns). Very few broken particles were observed.

Table 5 depicts the encapsulation efficiency of Comparative Example 2 and Inventive Example 3. Samples of each example were prepared by dispersing approximately 0.33 g of each Example in 10 mL of deionized water in a 50 mL centrifuge tube. The samples were vortexed for 20 seconds, roll mixed for 10 minutes, and then vortexed for another 20 seconds. The remaining percentage of encapsulated perfume oil was then evaluated by adding 20 mL of hexane or 20 mL of ethanol and centrifuging at 500 RPM for 1 minute to isolate the organic layer. The hexane or ethanol was then evaluated with gas chromatography and mass spectroscopy to determine the percentage of perfume oil extracted. For extraction with ethanol, each sample was heated to 60° C. for 30 minutes after addition of ethanol but before centrifuging.

TABLE 5

| Sample Description | % hexane extractable perfume oil | % ethanol extractable perfume oil |
| --- | --- | --- |
| Perfume Oil Control | 100% | 100% |
| Example 2 - Starch Encapsulated Perfume Oil without Phosphate Ester PA-900 | 100% | 100% |
| Example 3 - Starch Encapsulated Perfume Oil with Phosphate Ester PA-900 | 23% | 82% |

Example 4

Example 4 evaluates the use of different core materials by determining their miscibility with a suitable phosphate ester (PA-900 from Lakeland Laboratories Ltd.) Samples A to L were formed of two samples each of: glycerin; polyethylene glycol 400 ("PEG 400"); Dow Corning 200 Fluid (polydimethylsiloxane); menthol/menthyl lactate 50/50 mixture; isopropyl myristate (obtained from IFF); and permethyl 101a (obtained from Preperse Corp.).

TABLE 6

| Sample | Glycerin (g) | PEG 400 (g) | Dow Corning 200 Fluid (g) | Menthol/ Menthyl Lactate (g) | IPM (g) | Permethyl 101a (g) | PA-900 (g) | Comments |
| --- | --- | --- | --- | --- | --- | --- | --- | --- |
| A | 9.127 | | | | | | 1.060 | Cloudy dispersion; 1 single phase |
| B | 9.467 | | | | | | 0.603 | Cloudy dispersion; 1 single phase |
| C | | 9.014 | | | | | 1.067 | transparent solution, clear white, 1 phase; agitation introduces haze |

TABLE 6-continued

| Sample | Glycerin (g) | PEG 400 (g) | Dow Corning 200 Fluid (g) | Menthol/ Menthyl Lactate (g) | IPM (g) | Permethyl 101a (g) | PA-900 (g) | Comments |
|---|---|---|---|---|---|---|---|---|
| D | 9.704 | | | | | | 0.484 | transparent solution, clear white, 1 phase; agitation introduces haze |
| E | | 9.189 | | | | | 1.038 | fully miscible, 1 phase, transparent, homogeneous, clear white |
| F | | | 9.866 | | | | 0.524 | fully miscible, 1 phase, transparent, homogeneous, clear white |
| G | | | | 9.025 | | | 1.030 | fully miscible, 1 phase, transparent, homogeneous, clear white |
| H | | | | 9.528 | | | 0.645 | fully miscible, 1 phase, transparent, homogeneous, clear white |
| I | | | | | 9.001 | | 1.024 | fully miscible, 1 phase, transparent, homogeneous, clear white |
| J | | | | | 9.545 | | 0.701 | fully miscible, 1 phase, transparent, homogeneous, clear white |
| K | | | | | | 9.036 | 1.122 | fully miscible, 1 phase, transparent, homogeneous, clear white |
| L | | | | | | 9.518 | 0.574 | fully miscible, 1 phase, transparent, homogeneous, clear white |

As depicted by Table 6, the miscibility of the core materials is not determined by polarity. For example, menthol/menthyl lactate was fully miscible in the phosphate ester despite being a polar compound.

Example 5

Microcapsules having various core materials were formed. Sample 1 includes a perfume oil core, Sample 2 includes a Dow Corning 200 silicone fluid core, and Sample 3 includes a 50/50 blend of menthol and menthyl lactate core. Each sample was formed by mixing the lipophilic core with a polyethyleneimine aqueous solution. The polyethyleneimine aqueous solution was formed of 70.0 grams Luprasol WF (obtained from BASF Chemical Co.) and 630.3 g deionized water. Microcapsules of each sample were formed by mixing the following solutions with the polyethyleneimine aqueous solution depicted in Table 7.

The lipophilic core of Sample 1 included 3.21 g of phosphate ester PA-900 (obtained from Lakeland Laboratories Ltd.) and 12.82 g of perfume oil.

The lipophilic core of Sample 2 was formed of 3.4 g of phosphate ester PA-900 (obtained from Lakeland Laboratories Ltd.) and 12.80 of Dow Corning 200 silicone fluid.

The lipophilic core of Sample 3 was formed of 3.48 g of phosphate ester PA-900 (obtained from Lakeland Laboratories Ltd.) and 3.48 g of a 50/50 blend of menthol and menthyl lactate.

TABLE 7

| Sample | Core Material Description | Actual Core Material (g) | Solution Z (g) | Microscopy |
|---|---|---|---|---|
| 1 | Perfume Oil | 5.052 | 100.053 | Capsules observed |
| 2 | Silicone 200 Fluid | 5.072 | 100.041 | Capsules observed |
| 3 | Menthol/ Menthyl Lactate | 4.933 | 100.019 | Capsules observed |

As depicted by Table 7, each of the core materials was successfully encapsulated by the phosphate ester microencapsulation process.

Starch delivery vehicle samples were produced using a spray drying process. The microcapsule samples were formed from the following solutions:

Solution A: 14.987 g phosphate ester PA-900 (obtained from Lakeland Chemical Ltd.) and 85 g Apple Bloom Mod 5 fragrance oil.

Solution B: 625.353 g of HICAP 100 starch (obtained from Ingredion) and 1,878 g water heated to 70° C.

Solution C: 75.68 g chitosan (obtained as TCI C2395 from TCI America) and 2,425 g deionized water.

Solution D: 360.69 g epomin P-1050 (50% aqueous solution of polyethyleneimine obtained from Nippon Shokubai Co. Ltd) and 1439.48 g deionized water.

Solution E: 10 g calcium chloride dihydrate and 90 g deionized water.

Starch delivery vehicle Sample 4 was produced by adding 10.033 g of Solution A to 240.14 g of Solution B while mixing at 760 RPM using a pitched blade turbine agitator for 1 minute. 1000.26 g of Solution C was then added at the same agitation for 1 minute. The resulting slurry was spray dried using a co-current Niro A/S dryer with a diameter of 3 feet and an inlet air temperature 200° C. and an outlet air temperature of 100° C., a dryer vacuum of −230 millimeters of water, and centrifugal wheel atomization at 5.0 bar.

Starch delivery vehicle Sample 5 was produced by adding 10.012 g of Solution A to 240.08 g of Solution B while mixing at 760 RPM using a pitched blade turbine agitator for 1 minute. 300 g of Solution D was then added at the same agitation for 1 minute. The resulting slurry was spray dried using a co-current Niro A/S dryer with a diameter of 3 feet and an inlet air temperature 200° C. and an outlet air temperature of 100° C., a dryer vacuum of −230 millimeters of water, and centrifugal wheel atomization at 5.0 bar.

Starch delivery vehicle Sample 6 was produced by adding 10.03 g of Solution A to 230.35 g of Solution B while mixing at 760 RPM using a pitched blade turbine agitator for 1 minute. 998.59 g of Solution C was then added at the same agitation for 1 minute. Finally, 25.147 g of Solution E was added at the same agitation and mixed for one minute. The resulting slurry was spray dried using a co-current Niro A/S dryer with a diameter of 3 feet and an inlet air temperature 200° C. and an outlet air temperature of 100° C., a dryer vacuum of −230 millimeters of water, and centrifugal wheel atomization at 5.0 bar.

Starch delivery vehicle Sample 7 was produced by adding 10.051 g of Solution A to 230.06 g of Solution B while mixing at 760 RPM using a pitched blade turbine agitator for 1 minute. 300 g of Solution D was then added at the same agitation for 1 minute. Finally, 25.08 g of Solution E was added at the same agitation and mixed for one minute. The resulting slurry was spray dried using a co-current Niro A/S dryer with a diameter of 3 feet and an inlet air temperature 200° C. and an outlet air temperature of 100° C., a dryer vacuum of −230 millimeters of water, and centrifugal wheel atomization at 5.0 bar.

Starch delivery vehicle Sample 8 was produced by adding 20.012 g of Solution A to 720.1 g of Solution B while mixing at 760 RPM using a pitched blade turbine agitator for 1 minute. The resulting slurry was spray dried using a co-current Niro A/S dryer with a diameter of 3 feet and an inlet air temperature 200° C. and an outlet air temperature of 100° C., a dryer vacuum of −230 millimeters of water, and centrifugal wheel atomization at 5.0 bar.

Starch delivery vehicle Sample 9 was produced by adding 15.53 g of Solution A to 542 g of Solution B while mixing at 760 RPM using a pitched blade turbine agitator for 1 minute. 39.08 g of Solution E was then added at the same agitation for 1 minute. The resulting slurry was spray dried using a co-current Niro A/S dryer with a diameter of 3 feet and an inlet air temperature 200° C. and an outlet air temperature of 100° C., a dryer vacuum of −230 millimeters of water, and centrifugal wheel atomization at 5.0 bar.

The weight percentages of Starch delivery vehicle Samples 4 to 9 are depicted in Table 14. Starch delivery vehicle Sample 8 is comparative because it does not include a multivalent ion to cause precipitation of the phosphate ester and did not form stable microcapsules.

TABLE 14

| Material | Starch Delivery Vehicle Sample # | | | | | |
|---|---|---|---|---|---|---|
| | 4 | 5 | 6 | 7 | 8 | 9 |
| Fragrance Oil | 8.50% | 8.50% | 8.50% | 8.50% | 8.50% | 8.50% |
| Phosphate Ester PA-900 | 1.50% | 1.50% | 1.50% | 1.50% | 1.50% | 1.50% |
| HICAP 100 Starch | 60.00% | 60.00% | 57.50% | 57.50% | 90.00% | 87.50% |
| Chitosan | 30.00% | 0.00% | 30.00% | 0.00% | 0.00% | 0.00% |
| Epomin P Polyethyleneimine | 0.00% | 30.00% | 0.00% | 30.00% | 0.00% | 0.00% |
| Calcium Chloride | 0.00% | 0.00% | 2.50% | 2.50% | 0.00% | 2.50% |
| Water | 0.00% | 0.00% | 0.00% | 0.00% | 0.00% | 0.00% |

Starch Delivery Vehicle Samples 4 to 7 and 9 were also examined using microscopy.

Starch delivery vehicle Sample 4: A very thin membrane was observed in the few smooth morphology starch delivery vehicles that had cracks. Wrinkled particles had a much higher nitrogen content (indicating there is a higher fraction of chitosan in this morphology). Small areas were found having a high local concentration of phosphate.

Starch delivery vehicle Sample 5: A more uniform morphology was observed with only one type of particle. All particles were slightly wrinkled. Overall, the starch delivery vehicle was more spherical in nature. Traditional matrix type of morphology was observed (wall of the particle has droplets surrounded by a matrix of polymer). Polyethyleneimine content is high in the matrix capsule.

Starch delivery vehicle Sample 6: A very thin membrane was observed in the few smooth morphology starch delivery vehicles that had cracks. A considerable number of fractured starch delivery vehicles were observed in this sample. The fractured starch delivery vehicles primarily exhibited a smooth morphology.

Starch delivery vehicle Sample 7: Two different types of morphology were observed—wrinkled and smooth. The particle size of the two morphologies were similar. Fractured capsules had high levels of calcium and phosphate. Nitrogen surrounds almost all of the particles, indicating the presence of polyethyleneimine.

Starch delivery vehicle Sample 9: Both smooth and wrinkled morphologies were observed. Some of the smooth morphology starch delivery vehicles were more brittle. Smooth morphology starch delivery vehicles were larger in size than the wrinkled starch delivery vehicles. There are many more wrinkled starch delivery vehicles vs. smooth starch delivery vehicles (80:20).

Starch delivery vehicle Samples 4 to 9 were included in the leave-on conditioner matrix of Example 14. The formulations of the leave-on conditioner are depicted in Table 15.

TABLE 15

| EXAMPLE | Starch Delivery Vehicle Description | Leave-on Conditioner Matrix (g) | Perfume or Microcapsule Sample (g) | Water (g) |
|---|---|---|---|---|
| 15-1 | Control - Perfume Oil | 22.642 | 0.229 | 2.057 |
| 15-2 | Starch Delivery Vehicle Sample 4 | 22.636 | 2.241 | — |

TABLE 15-continued

| EXAMPLE | Starch Delivery Vehicle Description | Leave-on Conditioner Matrix (g) | Perfume or Microcapsule Sample (g) | Water (g) |
|---|---|---|---|---|
| 15-3 | Starch Delivery Vehicle Sample 5 | 22.662 | 2.324 | — |
| 15-4 | Starch Delivery Vehicle Sample 6 | 22.644 | 2.302 | — |
| 15-5 | Starch Delivery Vehicle Sample 7 | 22.641 | 2.31 | — |
| 15-6 | Starch Delivery Vehicle Sample 8 | 22.645 | 2.349 | — |
| 15-7 | Starch Delivery Vehicle Sample 9 | 22.642 | 2.359 | — |

The Hair Switch Treatment method was used to apply the leave-on conditioner products onto hair. The hair was allowed to dry at ambient temperatures. After 4 hours, the hair switches were evaluated by 3 panelists. The results are depicted in Table 16.

TABLE 16

| Example | Starch Delivery Vehicle Sample | Description | Primavera Grade (4 hr) Pre-Comb/Post-Comb |
|---|---|---|---|
| 15-1 | Control - Perfume Oil | Control | 15/20 |
| 15-2 | Starch Delivery Vehicle Sample 4 | Starch/Chitosan/Perfume | 20/35 |
| 15-3 | Starch Delivery Vehicle Sample 5 | Starch/PEI/Perfume | 20/45 |
| 15-4 | Starch Delivery Vehicle Sample 6 | Starch/Chitosan/CaCl$_2$/Perfume | 15/20 |
| 15-5 | Starch Delivery Vehicle Sample 7 | Starch/PEI/CaCl$_2$/Perfume | 20/25 |
| 15-6 | Sample 8 | Starch/Perfume | 20/35 |
| 15-7 | Starch Delivery Vehicle Sample 9 | Starch/Perfume/CaCl$_2$ | 20/30 |

As depicted by Table 16, Comparative Example 15-1 formed without microcapsules does not result in a noticeable fragrance longevity in hair. Samples including the microcapsule, in contrast, exhibited improved fragrance release post-combing. Even though Comparative Sample 8 shows a comb through benefit from this test, it is not believed this would retain the fragrance long term (per Table 5 Example 2 versus Example 3).

Examples 17-1 Through 17-3

The following examples illustrated in Table 17 are formulation examples containing microcapsules and a starch delivery vehicle. Examples 17-1, 17-2, and 17-3 are anhydrous, antiperspirant compositions including a surfactant, Performathox 450 ethoxylate, a spray-dried polyacrylate microcapsules made by interfacial polymerization, wherein the microcapsules encapsulate a fragrance and a quantity of non-volatile oils and a starch delivery vehicle as described above.

Examples 17-1 and 17-2 can be prepared by a batch process by adding all of the raw materials (except aluminum zirconium trichlorohydrex glycine powder, fragrance, polyacrylate microcapsules, and starch encapsulated accord) to a mix tank, heating the materials to a temperature of 88° C. to melt the structurants, performathox 450 ethoxylate and other higher melting point ingredients, and maintaining that temperature until the ingredients are melted. Once melted, the batch is cooled to 70-75° C. and the aluminum zirconium trichlorohydrex glycine powder, fragrance, polyacrylate microcapsules and starch delivery vehicle are added to the tank. The batch is then mixed for at least 15 minutes before cooling to 50-55° C. and pouring into canisters.

Example 17-3 is prepared by a split stream process. In the hot stream tank, the waxes (stearyl alcohol, castor wax, ozokerite, behenyl alcohol), emollients (C12-15 Alkyl benzoate), performathox 450 ethoxylate and a lesser portion of the cyclopentasiloxane are added into one tank, mixed, and then heated to 88° C. to melt the waxes. In the cold stream tank, the powders (actives, talc, cyclodextrins, spray-dried microcapsules, starch delivery vehicle), fragrances, PPG-14 butyl ether, and a greater portion of the cyclopentasiloxane are added and mixed and maintained at a temperature of less than 50° C. Once each of the hot and cold streams each is relatively homogenous, each of the process streams are simultaneously fed into a static mixer where the two streams are combined for about 5 seconds or less, ensuring a homogenous personal care composition while minimizing the mix time above the wax crystallization temperature. The antiperspirant composition then exits the static mixer into individual canisters where the product is allowed to cool to room temperature.

TABLE 17

| | Example 17-1 Soft Solid made via batch process | Example 17-2 Invisible Solid made via batch process | Example 17-3 Invisible Solid made via Split Stream |
|---|---|---|---|
| Aluminum Zirconium Trichlorohydrex Glycine Powder | 26.5 | 24.0 | — |
| Aluminum Zirconium Tetrachlorohydrex Gly | — | — | 25.6 |
| Cyclopentasiloxane | QS | QS | QS |
| Dimethicone | 5 | 5 | 5 |
| CO-1897 Stearyl Alcohol NF | — | 12.3 | 13.25 |
| Ozokerite Wax SP-1026 Type | — | 1.0 | 1.0 |
| Hydrogenated Castor Oil MP80 Deodorized | — | 2.75 | 2.90 |
| Behenyl Alcohol | — | 0.2 | 0.2 |
| Tribehenin | 4.5 | — | — |
| C 18-36 acid triglyceride | 1.125 | — | — |

TABLE 17-continued

| | Example 17-1 Soft Solid made via batch process | Example 17-2 Invisible Solid made via batch process | Example 17-3 Invisible Solid made via Split Stream |
|---|---|---|---|
| C12-15 Alkyl Benzoate | — | 8.5 | 8.5 |
| Performathox 450 ethoxylate | 1.0 | 1.0 | 2.0 |
| PPG-14 Butyl Ether | 0.5 | 6.5 | 6.5 |
| White Petrolatum | 3 | 3 | 3 |
| Mineral Oil | — | 8.0 | 8.0 |
| Fragrance | 0.75 | 0.75 | 0.75 |
| Talc Imperial 250 USP | — | 3 | 2.5 |
| Fragrance Complexed Beta-cyclodextrin | 2.0 | 3.0 | — |
| Polyacrylate Microcapsule | 2.0 | — | 2.0 |
| Starch Delivery Vehicle | 1.0 | 0.8 | 1.5 |

QS - indicates that this material is used to bring the total to 100%.

Examples/Combinations

A. An anhydrous antiperspirant composition comprising an antiperspirant active and a starch delivery vehicle, comprising: a starch, a core material, and a lipophilic phosphate ester; wherein the lipophilic phosphate ester at least partially coats the core material.

B. The anhydrous antiperspirant composition of paragraph A, wherein the lipophilic phosphate ester comprises a phosphate alcohol ester.

C. The anhydrous antiperspirant composition of paragraphs A-B, wherein the lipophilic phosphate ester comprises a phosphate diester.

D. The anhydrous antiperspirant composition of paragraphs A-C, wherein the lipophilic phosphate ester has an acid value of 180 mg KOH/g phosphate ester to 450 mg KOH/g phosphate ester.

E. The anhydrous antiperspirant composition of paragraphs A-D, wherein the lipophilic phosphate ester comprises an R-group having a carbon chain length of 6 to 18 carbons.

F. The anhydrous antiperspirant composition of paragraph E, wherein the R-group is a $C_8$ to $C_{10}$ linear alkyl chain.

G. The anhydrous antiperspirant composition of paragraphs A-F, wherein the lipophilic phosphate ester comprises a combination of phosphate monoesters and phosphate diesters, of $C_6$-$C_{16}$ alkyl phosphate esters and/or $C_6$-$C_{16}$ ethoxylated alkyl phosphate esters.

H. The anhydrous antiperspirant composition of paragraph G, wherein the of $C_6$-$C_{16}$ alkyl phosphate esters comprise 2-ethylhexyl phosphate ester, decyl phosphate ester, hexadecyl phosphate ester, octyl phosphate ester, lauryl phosphate ester, or a combination thereof.

I. The anhydrous antiperspirant composition of paragraphs A-H, wherein the starch comprises dextrin, pullulan, tapioca starch, starch acetate, maize starch, hydroxypropyl di-starch glycerol, hydroxyethyl starch, carboxymethyl starch, carboxyethyl starch, starch-2-hydroxypropyl citrate, starch sodium octenyl succinate, octenylsuccinic acid anhydride starch, or a combination thereof.

J. The anhydrous antiperspirant composition of paragraphs A-I, wherein the starch comprises an octenylsuccinic acid anhydride modified starch.

K. The anhydrous antiperspirant composition of paragraphs A-J, wherein the benefit agent comprises perfume, the starch comprises an octenylsuccinic acid anhydride modified starch, and the lipophilic phosphate ester comprises an octyl phosphate ester.

L. An anhydrous antiperspirant composition, comprising an antiperspirant active, and a starch delivery vehicle comprising a starch, a perfume, and a lipophilic phosphate ester; wherein the lipophilic phosphate ester at least partially coats the perfume and the perfume is miscible with the lipophilic ester.

M. The anhydrous antiperspirant composition of paragraph L, wherein the starch comprises dextrin, pullulan, tapioca starch, starch acetate, maize starch, hydroxypropyl di-starch glycerol, hydroxyethyl starch, carboxymethyl starch, carboxyethyl starch, starch-2-hydroxypropyl citrate, starch sodium octenyl succinate, octenylsuccinic acid anhydride starch, or a combination thereof.

N. The anhydrous antiperspirant composition of paragraphs L-M, wherein the lipophilic phosphate ester comprises a phosphate monoester, a phosphate diester, or a combination thereof.

O. The anhydrous antiperspirant composition of paragraphs L-N, wherein the lipophilic phosphate ester comprises has an acid value of 180 mg KOH/g phosphate ester to 450 mg KOH/g phosphate ester.

P. The anhydrous antiperspirant composition of paragraphs L-O, wherein the lipophilic phosphate ester comprises an R-group having a carbon chain length of 6 to 18 carbons.

Q. The anhydrous antiperspirant composition of paragraph P, wherein the R-group is a C8 to C10 linear alkyl chain.

R. The anhydrous antiperspirant composition of paragraphs L-Q, wherein the lipophilic phosphate ester comprises an octyl phosphate ester.

S. The anhydrous antiperspirant composition of paragraphs L-R, wherein the starch comprises an octenylsuccinic acid anhydride modified starch.

T. An antiperspirant composition comprising an antiperspirant active, and a starch perfume delivery vehicle comprising an octenylsuccinic acid anhydride modified starch, a perfume, and an octyl phosphate ester, wherein the octyl phosphate ester at least partially coats the perfume and is a reaction product of the octyl phosphate ester and a multivalent ion, and wherein the perfume is miscible in the octyl phosphate ester.

Method
Hair Switch Treatment Method

In a Hair Switch Treatment method, moderately damaged general population hair from International Hair Importers was obtained and made into hair switches of the following size: 4 grams and 8 inches. The hair switches are then stored with foil, tissue paper, or a kim wipe. Paper towels can contain silicone and are therefore, not used to avoid any additional contamination to the hair.

Test Set-Up: Preparation/Labeling
Hair Switches

Depending on the number of switches per product that is requested (standard is 2), hair switches should be labeled to correspond with the product sample codes. Marked switches are then hung on a cart in corresponding order.

Switch Treatment Conditions:

1. Constant Water Temperature

A temperature gauge should be installed at the sink to ensure a constant temperature throughout the treatment portion of the test. The standard temperature should be set at 100 degrees F.+/−3 degrees F.

2. Constant Water Pressure

The pressure of the rinse water must be regulated for rinsing consistency. A flow meter should be installed at the sink and adjusted to standard measurement of 1.5 gallons per minute+/−0.25 gpm.

3. Water Hardness—an average of 7-13 grain.

4. Milking and Rinsing Guidelines—milk at a rate of 50-60 strokes per 30 seconds. The milking procedure (stroking motion from top to bottom) is very critical to achieving consistent results from each switch within the confines of a product. A consistent milking pattern, maintaining that pattern and a constant rhythm throughout the treatment of all switches is critical. Milk the switch hard enough to allow the product to come in contact with the hair through its thickness and not just the outer layers.

5. A stationary shower rinse is used with no additional manipulation of the hair for 30 seconds. Lightly squeegee once down the switch from top to bottom between fingers after rinsing to remove excess water.

Treatment Procedure—1 Cycle

1) Wear vinyl gloves during the treatment process changing between every switch.
2) Use a separate 1 cc disposable syringe for each product application.
3) Standard product amount: 0.1 cc (equivalent to approximately 0.1 grams) per gram of hair.
4) Avoid contamination: handle switches by taped top and avoid contact with other switches/surfaces.
5) Pull up required product amount into syringes for each test product (make sure no air bubbles are in the syringe).
6) When the product is a cream, apply conditioner product (0.10 cc per gram of hair) evenly from top to bottom starting 1 inch down from the clamp using a 1 ml disposable syringe.
   a. Milk 50-60 strokes/30 seconds.
   b. Then hang on drying cart at ambient temperature and approximately 30% relative humidity.
7) When the product is a spray, prepare the hair switch in the following manner:
   a. Zero a large weigh boat with a 10 gram, 10 inch hair switch on the scale.
   b. Bring hair switch to sink, spray to cover length of switch. Spray should be roughly 6 inches from the switch while spraying.
   c. Start with 2 sprays front and back (total of 4), covering evenly top to bottom on each side.
   d. Weigh, and add more sprays as needed.
   e. Weigh: confirm that ~1 gram of product has been applied to hair (±10%).
   f. If under, apply additional product 1 spray at a time and measure (alternating sides of the switch for each additional spray).
   g. If over, get new switch.
   h. Comb to detangle—~3 combs on front, starting from bottom and working up (or as many combs as needed to untangle the hair).
   i. Then hang on drying cart at ambient temperature and approximately 30% relative humidity.

Olfactive Analysis Method

Once switches have been treated according to the Hair Switch Treatment method, the switches should be allowed to dry for at least 4 hours at 70° F./30% RH:

1) A perfumer or trained panelist assesses the fragrance on the hair switch by bringing the middle portion of the hair switch to the nose, and making an olfactive assessment. The Primavera olfactive grade is recorded as "initial pre-comb".
2) Next, a perfumer or trained panelist combs the hair switch 3× with the fine tooth side of a comb (11 cm long—teeth to teeth, 1.5 cm long teeth, teeth spaced approximately 0.10 cm apart), and then brings the middle portion of the hair switch to the nose, and makes an olfactive assessment. The Primavera olfactive grade is recorded as "initial post-comb".
3) In this manner, multiple combing sequences can be completed at different time points, using the same hair switch, in order to collect perfume intensity data.
4) The olfactive intensity scale ratings are given below.

| Olfactive Grade | Concentration of DihydroMyrcenol in mineral oil | Descriptors |
| --- | --- | --- |
| 0 | 0% | No Odor |
| 25 | 0.005% | Weak |
| 50 | 0.2% | Moderate |
| 75 | 2% | Strong |
| 100 | 100% | Very Strong |

A difference of 5 points on this scale is not considered a noticeable difference on hair. A 10 point difference in olfactive grade is large and noticeable.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An antiperspirant composition comprising an antiperspirant active, and a starch perfume delivery vehicle comprising an octenylsuccinic acid anhydride modified starch, a perfume, and an octyl phosphate ester, wherein the octyl phosphate ester at least partially coats the perfume and is a reaction product of the octyl phosphate ester and a multivalent ion, and wherein the perfume is miscible in the octyl phosphate ester.

2. The antiperspirant composition of claim 1, wherein the antiperspirant composition is anhydrous.

3. The antiperspirant composition of claim 1, wherein the octyl phosphate ester has an acid value below about 950 mg KOH/g phosphate ester.

4. The antiperspirant composition of claim 1, wherein the octyl phosphate ester has an acid value of about 180 mg KOH/g phosphate ester to about 450 mg KOH/g phosphate ester.

5. The antiperspirant composition of claim 1, wherein the perfume and octyl phosphate ester form a lipophilic phase in which the perfume forms from about 60% to about 90% of the lipophilic phase.

6. The antiperspirant composition of claim 1, wherein the multivalent ion is selected from the group consisting of calcium chloride, aluminum sulfate, chitosan, polyethyleneimine ("PEI") and polydiallyldimethylammonium chloride ("polyDADMAC").

7. The antiperspirant composition of claim 1, wherein the perfume has a ClogP value of about 1 to about 5.

8. The antiperspirant composition of claim 1, wherein the perfume has a ClogP value of about 3 to about 4.5.

9. The antiperspirant composition of claim 1, wherein the antiperspirant active comprises aluminum.

* * * * *